US011181522B2

(12) United States Patent
Wan et al.

(10) Patent No.: US 11,181,522 B2
(45) **Date of Patent: *Nov. 23, 2021**

(54) ANALYTICAL CARTRIDGE WITH FLUID FLOW CONTROL

(71) Applicant: MicroPoint Bioscience Inc., Santa Clara, CA (US)

(72) Inventors: Zhiliang Wan, Milpitas, CA (US); Nan Zhang, Cupertino, CA (US)

( * ) Notice: Subject to any disclaimer, the term of this patent is extended or adjusted under 35 U.S.C. 154(b) by 576 days.

This patent is subject to a terminal disclaimer.

(21) Appl. No.: 16/008,542

(22) Filed: Jun. 14, 2018

(65) Prior Publication Data

US 2018/0372739 A1 Dec. 27, 2018

Related U.S. Application Data

(60) Continuation of application No. 14/029,215, filed on Sep. 17, 2013, now Pat. No. 10,001,479, which is a (Continued)

(51) Int. Cl.

*G01N 33/558* (2006.01)
*B01L 3/00* (2006.01)

(52) U.S. Cl.

CPC ...... *G01N 33/558* (2013.01); *B01L 3/502746* (2013.01); *B01L 3/502753* (2013.01); *B01L 2200/04* (2013.01); *B01L 2200/0631* (2013.01); *B01L 2200/16* (2013.01); *B01L 2300/069* (2013.01); *B01L 2300/0654* (2013.01); *B01L 2300/0819* (2013.01);

(Continued)

(58) Field of Classification Search

None

See application file for complete search history.

(56) References Cited

U.S. PATENT DOCUMENTS 4,756,884 A 7/1988 Hillman et al.
5,110,724 A 5/1992 Hewett (Continued)

FOREIGN PATENT DOCUMENTS

EP 1 571 446 A1 9/2005
EP 1 635 170 A1 3/2006

(Continued)

OTHER PUBLICATIONS

European Search Report dated Oct. 19, 2012 for application No. 09794760.0.

Wkiapedia, diameter of blood cells is between 8-8 microns, 2012.

*Primary Examiner* — Lyle Alexander
*Assistant Examiner* — Bryan Kilpatrick
(74) *Attorney, Agent, or Firm* — BioPatent; Gary Baker

(57) ABSTRACT

Analytical cartridges, systems and methods of processing a sample for analysis using capillary flows. Vertical gradient sample filtration provides filtrate to an incubation chamber for a time controlled by a flow modulator at the outlet of the incubation chamber. The flow modulator can include a serpentine capillary flow path without side walls. Incubated filtrate can flow from the incubation chamber to a detection channel after a predetermined time. The detection chamber can include one or more analytical regions in a porous substrate for detection of two or more analytes on the same cartridge from the same sample.

14 Claims, 5 Drawing Sheets

Related U.S. Application Data division of application No. 13/608,408, filed on Sep. 10, 2012, now Pat. No. 8,551,422, which is a division of application No. 12/456,247, filed on Jun. 12, 2009, now Pat. No. 8,263,024.

(60) Provisional application No. 61/210,989, filed on Mar. 24, 2009, provisional application No. 61/134,459, filed on Jul. 9, 2008.

(52) U.S. Cl.
CPC .................. *B01L 2300/0883* (2013.01); *B01L 2300/0887* (2013.01); *B01L 2300/165* (2013.01); *B01L 2400/0406* (2013.01); *Y10T 137/0318* (2015.04)

(56) References Cited

U.S. PATENT DOCUMENTS

| | | | |
|---|---|---|---|
| 6,391,265 B1 | 5/2002 | Buechler et al. | |
| 6,436,716 B1 | 8/2002 | Wu | |
| 6,821,485 B2 | 11/2004 | Beebe et al. | |
| 6,905,882 B2 | 6/2005 | Buechler | |
| 7,334,893 B2 | 2/2008 | Altheimer et al. | |
| 7,347,972 B1 | 3/2008 | Lee | |
| 8,551,422 B2 * | 10/2013 | Wan | B01L 3/502753 422/503 |
| 2003/0124738 A1 | 7/2003 | Crosby | |
| 2004/0063197 A1 | 4/2004 | Tilles et al. | |
| 2005/0130293 A1 | 6/2005 | Blatt et al. | |
| 2005/0196875 A1 | 9/2005 | Blatt et al. | |
| 2005/0249633 A1 | 11/2005 | Blatt et al. | |
| 2006/0078986 A1 | 4/2006 | Ly et al. | |
| 2007/0031283 A1 * | 2/2007 | Davis | A61B 5/150221 422/400 |
| 2007/0081920 A1 | 4/2007 | Murphy et al. | |
| 2009/0227041 A1 | 9/2009 | Wang et al. | |

FOREIGN PATENT DOCUMENTS

| | | |
|---|---|---|
| WO | WO 2005/090987 | 9/2005 |
| WO | WO 2005/116632 | 12/2005 |

* cited by examiner

ANALYTICAL CARTRIDGE WITH FLUID FLOW CONTROL

CROSS-REFERENCE TO RELATED APPLICATIONS

This application is a Continuation application from parent Ser. No. 14/029,215, which is a Divisional application from parent application Ser. No. 13/608,408, filed Sep. 10, 2012, which claims benefit of application Ser. No. 12/456,247 (now U.S. Pat. No. 8,263,024), filed Jun. 12, 2009, and claims benefit of and priority to prior U.S. Provisional Application No. 61/210,989, Analytical Cartridge with Fluid Control Applications, by Zhiliang Wan, et al., filed Mar. 24, 2009; and prior U.S. Provisional Application No. 61/134,459, Analytical Cartridge with Fluid Control Applications, by Zhiliang Wan, et al., filed Jul. 9, 2008. The full disclosure of the prior application is incorporated herein by reference.

FIELD OF THE INVENTION

The invention is in the field of capillary and microfluidic cartridges and methods of their use. The cartridges can include filter elements providing sample filtrate to an incubation chamber with residence time controlled by a flow modulator channel. The flow modulator can release incubated filtrate to one or more analytical regions of the cartridge where incubation product can interact with reagents and/or be detected. The flow modulator can have a serpentine flow path between two surfaces without the need to include solid path side walls. The analytical region can include a porous substrate, not occluding the channel cross-section, e.g., retaining reagents to interact with analytes or reaction products from the incubation chamber. The methods can include introducing a liquid sample to the cartridge to flow and incubate in a chamber with a residence time controlled by a restricted exit flow through a serpentine flow path not enclosed in a channel having side walls.

BACKGROUND OF THE INVENTION

Fluid flow control through microfluidic and capillary devices has been problematic. Application of macro-scale flow control techniques, such as, e.g., mechanical valving and discrete pumping, can be complex, expensive, difficult to manufacture, and poorly functional in micro-scale applications. Some micro-scale cartridges address flow control issues using wicking, centrifugation, hydrophobic treated surfaces, electrowetting, and the like, to influence flow of fluids through cartridge channels. Still, problems arise or remain in many micro-flow applications.

Many samples of interest, e.g., in bioassays include substantial amounts of particulate that must be removed to prevent interference in the assay reactions and to avoid clogging of assay device channels. The use of filter materials to remove particulate is known in the prior art. For example, in one configuration, filters are provided with a long lateral flow path, such as is described in "Devices for Incorporating Filters for Filtering Fluid Samples", U.S. Pat. No. 6,391,265, to Buechler, et al. Buechler applies sample fluid to one end of a planar filter and collects filtrate at the other end of the same filter. However, this single filter technology has the disadvantage the same filter dealing with the gross particulate of the sample also has to handle the final fine filtration. Moreover, the long filter path can cause undue delay in filtration and loss of sample to excess dead volume.

Another issue often encountered in assay cartridges concerns how to control residence time in reaction chambers. It can be desirable to have sample flow quickly into contact with analytical reagents, but then linger for adequate mixing and completion of reaction kinetics. In some embodiments, flows can be stopped by increasing the contact angle of the fluid at the surface (e.g., by increasing the channel diameter or by coating the channel surface with a hydrophobic material), but the flows are not readily resumed without application of an external force. For example, electrowetting forces can be applied to resume flow, as disclosed in U.S. Pat. No. 7,117,807. Electro-capillarity or electrowetting (EW) is based on the observation that electrostatic forces can change surface tension of a fluid at a near-by surface. However, such control requires incorporation of electrodes and control electronics into the assay system. Alternately, as described in U.S. Pat. No. 6,905,882, a flow from a reaction chamber can be delayed by a time gate made up of a hydrophobic surface at the exit port of the chamber. Reaction product is released from the reaction chamber when the hydrophobic stop surface is rendered hydrophilic by constituents of the reaction liquid. However, consistent flow delay can require unchanging fluid compositions, consistent temperatures, consistent manufacturing, etc.

Retention of reagents on plastic surfaces of analytical cartridges can be a problem. The surfaces, e.g., of polystyrene, can have insufficient reagent concentration and too brief a residence time as analyte solutions flow past. In some cases reaction or detection regions have been stuffed full of capillary materials, however, this can overly inhibit flow and block viewing angles for detection devices.

Many assay cartridges are assembled by fusing several layered components. With such devices, it can be difficult to control leakage between layers or to control capillary creeping along interfaces of imperfectly fitting layers. Moreover, bubbles or particles in narrow channels between the layers can cause blockage.

Multi-assay concepts exist, but they are not optimized for the small sample size commonly encountered in the microfluidic or massive screening environments. For example in the multi-assay system of U.S. Pat. No. 7,347,972, completion of five different assays requires five times as much sample as one assay. In U.S. Patent application 2005/0249633, multiple assays require sample fluid to flow to multiple dead end arms of a branched channel system, requiring additional sample for each arm and setting the stage for problematic or impossible filling, rinsing and scanning for the isolated analytical regions of the cartridge.

In view of the above, a need exists for capillary/microfluidic cartridges that can readily and efficiently provide sample for analysis without particles. It would be desirable to have assay cartridges that can efficiently provide multiple analysis results from one small sample. It would be desirable to have restrictive flow channels that are not sensitive to blockage by bubbles. There would be benefits in cartridges with high reagent concentrations without flow restriction. A simple reaction chamber residence time controller that is easy to manufacture, without the need for high assembly tolerances, and without the need for input of external timing forces, would be appreciated in the art. The present invention provides these and other features that will be apparent upon review of the following.

SUMMARY OF THE INVENTION

The present inventions include methods, cartridges and systems for processing a liquid sample and detecting an analyte of interest. A sample can be applied to a transverse flow filter so the filtrate flows into an incubation chamber for preliminary conditioning and/or reactions. The filtrate can be retained in the incubation chamber by a flow modulator at the outflow port of the chamber for a time adequate to condition of react the filtrate. The incubated filtrate can ultimately flow through the flow modulator to contact one or more analytical regions in a downstream detection channel substrate. The analytical regions can be formed in a porous substrate, e.g., that does not play an important part in fluid flow along the axis of the detection channel (e.g., without substantial lateral flow). The analytical regions can, e.g., capture reaction products for detection and/or provide reagents for further reactions with filtrate constituents. In preferred embodiments, the flow modulator is a serpentine fluid flow path with open path sides. In many embodiments, the detection channel includes two or more analytical regions. Detection systems can include devices with a stage to receive the cartridges of the invention, preferably including a variable amplitude light source to illuminate the cartridge analytical regions.

Analytical cartridges of the invention can include, e.g., a filter element comprising a sample receiving surface and a filtrate egress surface, wherein the receiving surface comprises an average pore diameter greater than an average pore diameter of the egress surface. The cartridges further include, e.g., an incubation chamber in fluid contact with the filtrate egress surface, a flow modulator in fluid contact with the incubation chamber, and one or more analytical regions positioned along a detection channel in fluid contact with the flow modulator. In this configuration, a flow of a filtrate from the incubation chamber is slowed by the flow modulator to influence the residence time of the filtrate in the incubation chamber.

The sample filter element can be in a filter chamber and include a pore size gradient from larger pores to smaller pores in the direction of filtrate flow through the filter. For example, the filter element can include two or more filter layers comprising different average pore diameters. In preferred embodiments, the filtrate does not flow laterally through the filter element, but is flows primarily traversely through the filter element. In many embodiments, filtrate through the filter element contacts a hydrophilic pad or hydrophilic capillary grooves that expedite flow and direct filtrate flow toward the incubation chamber.

Flow modulators typically substantially slow the flow rate of filtrate from the incubation chamber into the detection channel, e.g., compared to the flow rate directly therebetween without the flow modulator. The flow path surface of the flow modulator is typically not more hydrophobic than the inner surfaces of the incubation chamber, but can be. In a preferred embodiment, the flow modulator has a flow path defined by opposing top and bottom flow path surfaces, and the flow path does not have solid side walls.

The detection channel can have a substrate disposed upon the channel surface with one or more analytical regions that function in capture, reaction, and/or detection of an analyte or analyte reaction product. The analytical regions typically each include one or more reagents associated (bound or not) with the substrate (porous or not). In some cases the analytical region has no reagent but a physical structure, such as a transparent surface, cooperating with detection system components. In some embodiments, the analytical regions each comprise a porous matrix analytical region substrate that does not fill the entire cross-section of the detection channel. For example, the detection channel can have a top surface and a bottom surface with an analytical region in a nitrocellulose substrate layer in contact with either the top surface or the bottom surface but not in contact with both surfaces. In a typical capillary scale embodiment, wherein the detection channel has a height of about 150 μm or less and the analytical regions are in a porous polymer layer less than 15 μm thick in contact with a surface of the detection channel. The detection chambers can include one, two or more analytical regions in a hydrophilic porous substrate. In most embodiments, the one or more analytical regions are not contiguous, but separated sequentially along the detection channel with a of non-analytical region space between, e.g., substrate not having an analytical region reagent. The analytical regions can be separately sequential along a strip of porous substrate or they can be located on a separate pieces of porous substrate material.

In a preferred embodiment, the analytical cartridge includes a detection channel having one or more capillary dimensions and one or more an analytical regions in the detection channel, wherein the one or more analytical regions comprise a porous substrate that does not fill a cross-section of the detection channel. For example, the detection channel of an assembled cartridge can have a height of 0.5 mm or less, while the porous substrate has a thickness of 0.2 mm or less. It is preferred that the cross sectional area of the one or more analytical regions is less than 50% of the total channel cross sectional area in a plane perpendicular to the channel axis. In use, a liquid (e.g., analyte solution, reagent and/or reaction product solution) typically flows along the detection channel by capillary action. The liquid typically does not flow significantly through the porous substrate by lateral flow. For example, most of the fluid flow is through the detection channel cross section not occupied by the porous substrate. The porous substrate can be any appropriate material for the particular analyses, but typical substrates include protein binding materials such as nitrocellulose, PVDF, hydrophilic porous polymers, and the like.

The cartridge in general can be formed in any suitable way. In many embodiments, the cartridge is prepared by assembly of two or more layers to form a laminated planar structure. In a preferred embodiment, cartridge has a less hydrophilic top cover overlying the filter element and a more hydrophilic surface overlying the incubation chamber, e.g., so that aqueous samples are less likely to flow between the filter and top cover, but tend to completely fill the incubation chamber. In many embodiments, the detection channel is formed between a cartridge top cover and a cartridge base using transparent materials allowing interrogation of analytical regions by an external detector light source.

The present inventions include, cartridge readers configured to detect a signal from an analytical region of the cartridges, wherein the reader comprises a laser with adjustable output intensity. In this way, detectable signal outputs from analytical regions can be modulated to provide an optimal sensitivity and/or range. In one aspect of the cartridges, a bar code can be provided to identify an appropriate laser intensity setting for illumination of analytical regions on that particular cartridge.

The present inventions include flow modulators having a flow path not sealed on one or more sides. For example, the cartridges can include a first chamber (e.g. an incubation chamber containing an analytical reagent), a flow modulator and a second chamber (e.g., a detection channel). The flow modulator can comprise a fluid flow path defined by opposing top and bottom path surfaces, but wherein the flow path does not have solid lateral side walls. In this configuration, a fluid flowing from the first chamber flows along the flow path, but surface tension of the fluid does not allow the fluid to flow laterally out from the flow path. For example, the fluid flow path is configured so that the fluid flows along the path by capillarity but a contact angle of the fluid at a lateral edge of the path prevents the fluid from flowing laterally from the flow path. The increased contact angle at the lateral edge of the flow path can result from an enlarged, non-capillary adjacent lateral space and/or provision of lateral surfaces with less affinity (e.g., more hydrophobic surfaces) for the fluid. It is preferred that the opposing path surfaces be substantially parallel and separated by a capillary scale path spacing distance. Optionally, the distance between the flow path upper and Lower surfaces can change, e.g., to smaller distances efferently or larger distances efferently. In preferred embodiments, the lateral space comprises upper and lower lateral space surfaces separated by a distance greater than the path spacing distance. It is preferred that flow path surfaces of the flow modulator are not more hydrophobic than an outlet surface from the first chamber or subject to being rendered more hydrophilic by a constituent of the filtrate or incubation reaction. It is notable that flow modulators can be configured to function in many ways, e.g., beyond simply slowing fluid flow rates. For example, the flow modulators can comprises an analytical reagent or a ligand capture moiety, e.g., to enable reaction or detection functions.

The present inventions include methods of controlling a fluid flow. For example, the methods can include providing a flow modulator having a fluid flow path defined by opposing top and bottom path surfaces, wherein the flow path does not comprise solid lateral side walls, and wherein the flow path comprises an inlet and an outlet; providing one or more lateral spaces adjacent to the flow path and in fluid contact along the flow path; and, introducing a fluid to the flow path inlet, so that the fluid flows along the flow path by capillary action. In this way, the contact angle of the fluid at the top and/or bottom lateral space prevents the fluid from flowing laterally from the flow path.

The methods can further include providing a first chamber and a second chamber in fluid contact through the flow modulator, and the step of introducing the fluid to the flow path inlet by introducing the fluid into the first chamber. The cartridge can be configured to flow the fluid into the first chamber at a first flow rate, and to flow fluid into the flow modulator as a second rate. In preferred embodiments, the rate of fluid flow along the modulator flow path is less than the first flow rate. However, the inventive methods can employ flow path configurations can provide a flow rate along the flow path that increases when the fluid exits the flow modulator at the outlet, as described herein.

The cartridges of the invention can include a flow modulator comprising a fluid flow path defined by opposing top and bottom path surfaces, wherein the flow path does not comprise solid lateral side walls, and a detection channel in fluid contact with the flow modulator and comprising two or more separate analytical regions along the detection channel.

DEFINITIONS

Unless otherwise defined herein or below in the remainder of the specification, all technical and scientific terms used herein have meanings commonly understood by those of ordinary skill in the art to which the present invention belongs.

Before describing the present invention in detail, it is to be understood that this invention is not limited to particular devices or biological systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "a component" can include a combination of two or more components; reference to "fluid" can include mixtures of fluids, and the like.

Although many methods and materials similar, modified, or equivalent to those described herein can be used in the practice of the present invention without undue experimentation, the preferred materials and methods are described herein. In describing and claiming the present invention, the following terminology will be used in accordance with the definitions set out below.

As used herein, a "flow modulator" refers to a structure that changes the flow rate (volume per unit time) of a fluid flowing between two channels and/or channels, with or without side walls, as discussed herein. In preferred embodiments of the invention, a flow modulator is a constriction in the flow path between two channels and/or channels (e.g., an incubation chamber and a detection channel of analytical regions), a relatively constricted conduit of some length between two channels and/or channels, or a flow path without side walls and having a relatively constricted cross section and running some distance between two channels and/or channels in an analytical cartridge of the invention.

A "lateral fluid flow path" in a planar filter runs substantially parallel to the planar surface. That is, a straight line drawn from the point of fluid sample application on the filter to the point where the bulk of the filtrate flow exits the filter in use runs generally parallel to (e.g., within 20°, 10°, 5°, or 2° of) the planar surface of the filter. For example, fluid typically flows in a lateral flow path through a filter paper sheet when filtrate is collected some distance from the point of application (besides a position near a point on the opposite side of the sheet); and would not be considered lateral flow when the filtrate is collected on the other side of the paper directly across the thickness from the point of application after a transverse flow. Of course, fluids applied to a filter will run in all directions, but the current definition is concerned with the overall bulk flow direction of the fluid. In the context of a porous substrate in a detection channel, lateral flow would typically exist where the substrate fills the channel cross section. However, where the substrate only fills a portion of the cross section, such as 50% or less, the majority of fluid will avoid the resistance of the substrate and flow outside the substrate so that lateral flow (substantially along the channel axis) through the substrate would typically not be significant.

A "transverse fluid flow path" in a planar filter runs substantially perpendicular to the planar surface. That is, a straight line drawn from the point of fluid sample application on the filter to the point where the bulk of the filtrate flow exits the filter in use runs generally parallel to (e.g., within 20°, 10°, 5°, or 2° of) a line perpendicular to the planar surface of the filter. For example, fluid flowing vertically through a planar filter element lying in a horizontal plane is an example of a transverse (not lateral) fluid flow through a filter. Of course, fluids applied to a filter will run in all directions, but the current definition is concerned with the overall bulk flow direction of the fluid.

As used herein, peripheral edges of planar cartridge elements are the thin surfaces exposing the thickness of the element, e.g., as in common usage of the term. As used herein, directional terms, such as "upper", "lower", "top", and "bottom" are as in common usage, e.g., with a planar cartridge disposed resting upon a table with the top cover above the base section. Height, width and depth dimensions are according to common usage, e.g., with reference to a cartridge major plane in a horizontal attitude.

As used herein, "substantially" refers to largely or predominantly, but not necessarily entirely, that which is specified.

The term "about", as used herein, indicates the value of a given quantity can include quantities ranging within 10% of the stated value, or optionally within 5% of the value, or in some embodiments within 1% of the value.

"Hydrophobic" and "hydrophilic" are relative terms. A first surface is more hydrophobic than a second surface if it has a higher affinity for lipids than the second surface, or repels water more than the second surface. The relative hydrophobicity of surfaces can be objectively determined, e.g., by comparing the contact angles of an aqueous solution on those surfaces. For example, if the contact angle of water is greater on the first surface than on the second surface, the first surface is considered more hydrophobic than the second surface.

As used herein, the term "microfluidic" refers to systems or devices having a fluid flow channel with at least one cross sectional dimension less than 1000 μm. Most microfluidic channels allow capillary flow, e.g., depending on the affinity of a particular fluid for the channel walls. Some functionally capillary scale channels can be greater than microfluidic scale. For example, a microfluidic channel can have a cross-sectional dimension of 500 μm or less, 300 μm or less, 100 μm or less, 50 μm or less, or 10 μm or less. In many embodiments, the channel dimension is about 50 μm to 100 μm, but typically not less than 1 μm. Valves of the invention can also be used in larger scale channels, such as capillary channels, which are channels wherein a fluid can flow by capillary action. Capillarity is a general term referring to phenomena attributable to the forces of surface or interfacial tension. A capillary scale chamber or channel has at least one dimension that functionally results in flow of an intended fluid along the chamber of channel surface by capillary action. Capillary scale chambers and channels of the invention can be at a microfluidic scale or not.

BRIEF DESCRIPTION OF THE DRAWINGS

FIG. 4B shows a serpentine flow path 40 can be formed between incubation chamber 14 and detection chamber 16. The path can be defined by path surface projections (e.g., defined by border surface recesses) from the top cover and/or base section. FIG. 4A is a partial sectional view of FIG. 4B.

DETAILED DESCRIPTION

The present inventions are directed generally to analytical cartridges and analytical methods. The cartridges can include a vertical transverse flow filter feeding filtrate to a detection channel through a reaction chamber; wherein flow between the reaction chamber and detection channel is influenced by a flow modulator component. The detection channel typically includes two or more separate analytical regions for detection of two or more different analytes. Analytical regions in the detection channel are typically situated in a porous substrate. The methods can include introduction of a sample to a filter providing filtrate flow to a reaction chamber with residence time controlled by a flow modulator comprising a flow path without entirely enclosing walls.

The cartridges include, e.g., vertical flow filter element having greater average pore size at the top sample-receiving surface than at the bottom sample filtrate egress surface. The filter element can be in the compartment in fluid contact with an incubation chamber, typically where a sample analyte reacts with an assay reagent under controlled conditions. The reaction mixture can be retained in the incubation chamber for a residence time dependent upon exit flow delays caused by a flow modulator structure, e.g., a narrower serpentine flow channel or flow path. Reaction product flow can continue to one or more analytical regions for detection of a signal proportional to the amount of analyte present in the original sample. Analyte of reaction products can be captured by or reacted with a reagent defining an analytical region in a porous substrate not filling the detection channel cross section.

The methods include, e.g., application of a sample for vertical depth filtration and incubation of the filtrate with reagents for a time controlled by a flow modulator at the outflow of the reaction chamber. The flow modulator can be configured with a fluid flow path defined by a pair of opposing upper and lower capillary surfaces. The lateral extent of the flow path can be defined without solid walls, e.g., by a lateral adjacent space not conducive to capillary flow from the intended flow path.

Analytical Capillary Flow Cartridges

Figure 1:
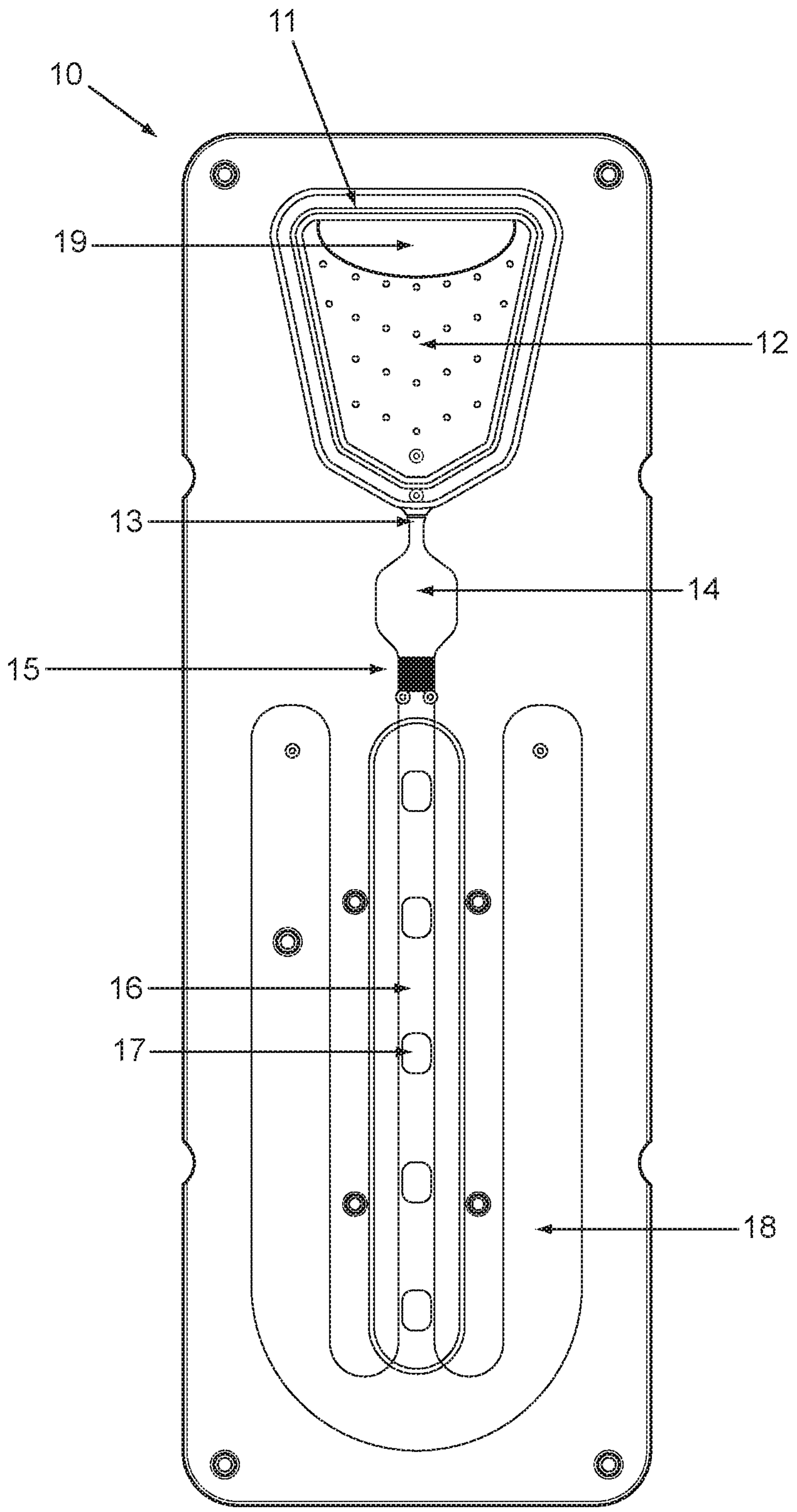
FIG. 1 is a schematic diagram of a typical assay cartridge of the invention, including sample filtration, reaction, detection and waste segments.

Cartridges of the invention can be, e.g., multi-assay cartridges receiving sample fluid through a vertical flow filter into a reaction reservoir for a time controlled by a flow modulator. For example, cartridge 10 can include compartments and channels in sequential fluid contact. As shown in FIG. 1, filter chamber 11 includes filter element 12 in fluid contact with incubation chamber 14 through back diffusion barrier 13. Exit of a fluid from the incubation chamber is regulated by flow modulator 15, which eventually releases reaction products from the incubation chamber into detection channel 16. The detection channel can include more than one analytical region 17 on a substrate where further reactions and/or detection can take place. Finally, the cartridge 10 can include one or more vented waste chambers 18 configured to receive expended sample, reagent, and/or rinse solutions, as required.

Figure 2:
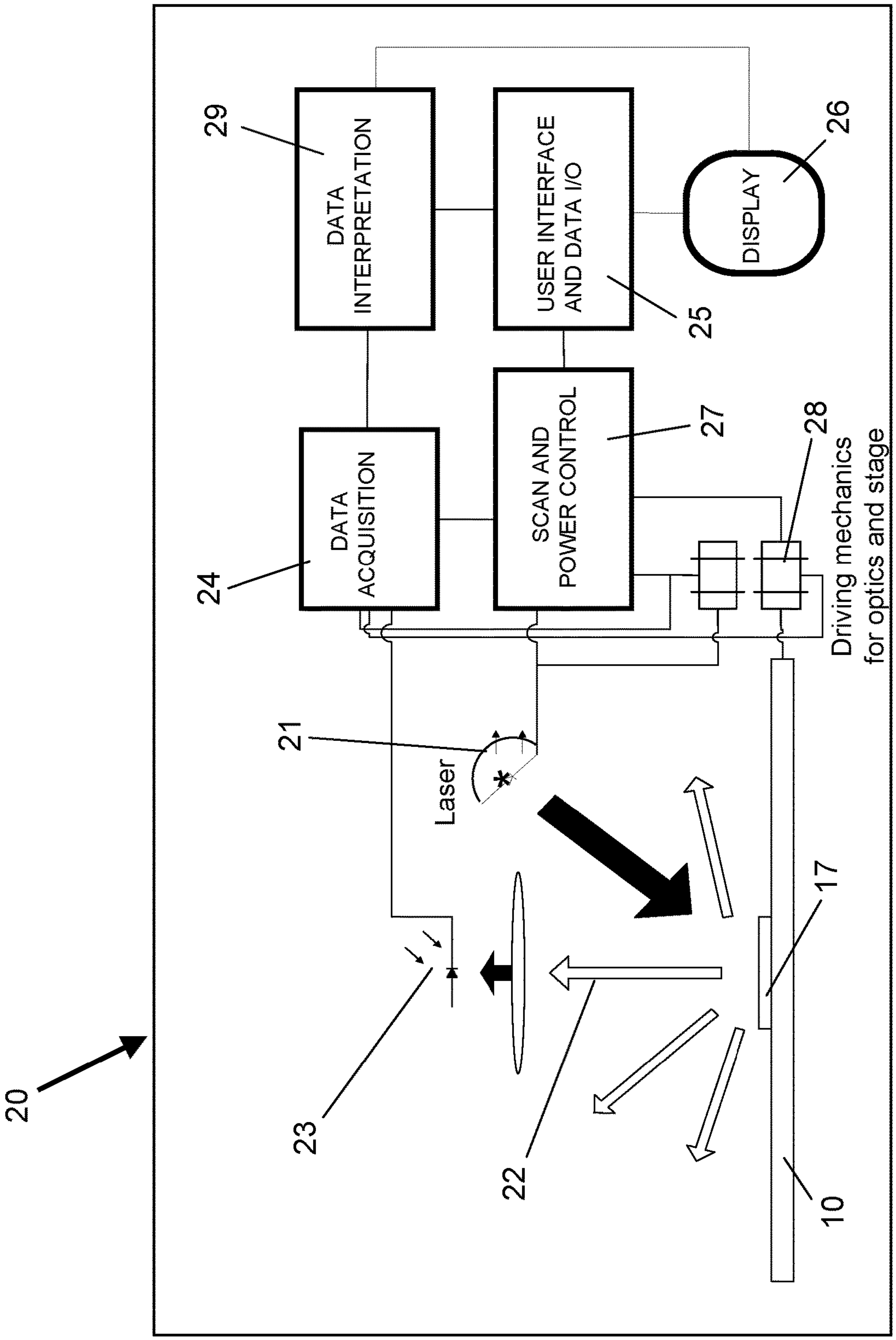
FIG. 2 is a schematic diagram of an assay reader system including the cartridge on a stage in a computer controlled device with detection by light interrogation and emissions detection.

In use, a complex sample, including particulate constituents and putative analytes, can be applied to the filter through sample loading inlet 19 where fluid flow through a linear or stepped gradient of decreasing pore sizes vertically can remove the particulates. Sample filtrate can flow to the incubation chamber by capillary action to contact an assay reagent in the incubation chamber. After reaction for an appropriate time, the bulk of the fluid can flow through the flow modulator to sequentially contact the analytical regions along the substrate of the detection channel. As shown in FIG. 2, the interaction between the reaction product fluid and assay components (e.g., bound second reagents) at the analytical regions can be detected by a detector system 20. For example, a light source 21 can illuminate an analytical region, which in turn can emit (e.g., transmit, fluoresce, reflect) light 22 of a quality and/or quantity related to the presence or absence of analyte in the original sample fluid. The light can be detected by a suitable detector 23, which transmits, e.g., a proportionate electric signal to a system data acquisition module 24 (e.g., analog to digital converter). The data can be interpreted by computer system 29 hardware and software. The computer can also include a user interface 25 and display 26. Multiple analyses can be detected in parallel (e.g., using a charge coupled device array) or assays can be read sequentially along the analytical regions, e.g., by reorientation of the cartridge 10 relative to the detector 23 and/or light source 21. The reorientation can be controlled by a computer scan and power control module interface to system drive mechanics 28 for the optics and/or cartridge stage.

Cartridge Structures

The typical cartridge of the invention is a structure made up from two or more laminated layers configured to provide ports, chambers, channels, surfaces and chemical constituents that functionally interact to allow detection of one or more analytes of interest.

Figure 3:
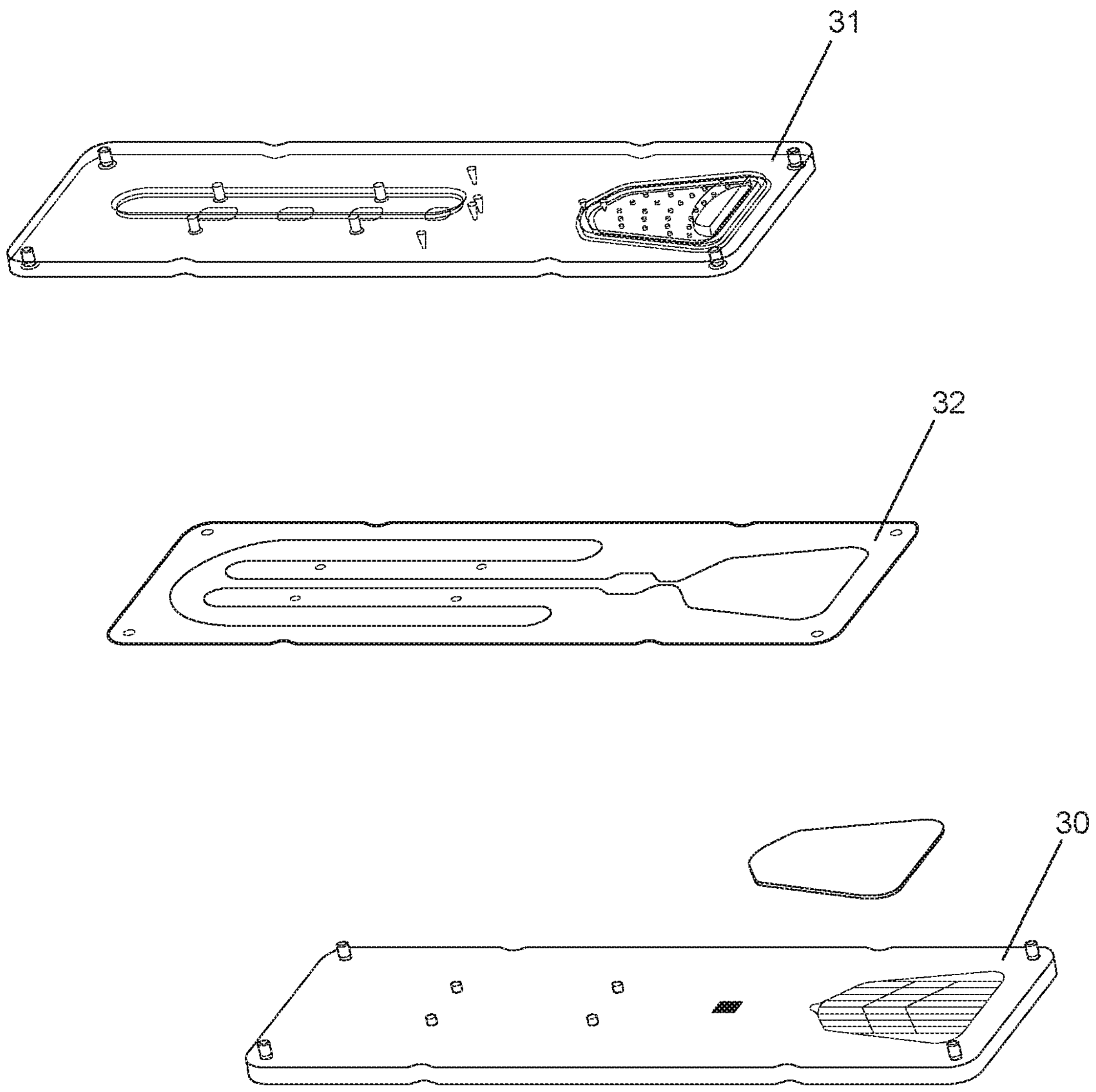
FIG. 3 is a schematic diagram depicting an exploded view of an exemplary layered cartridge assembly of a membrane spacer layer sandwiched between a base section and a cartridge top cover.

As shown in FIG. 3, a cartridge can be assembled in layers from a base section 30 and a top cover 31. The base and/or cover can have recesses on their surfaces that define fluid flow pathways, such as channels and chambers, when sandwiched together. Optionally, the cartridge can include a membrane layer 32, defining portions (e.g., side walls) of certain cartridge compartments.

In a preferred embodiment, the inner surface of the top cover is more hydrophobic than other parts of the cartridge. This can help prevent aqueous samples and/or reagents from flowing outside of the intended channels. For example, the top cover can be made from a more hydrophobic material than the base section. Optionally, the inner top cover can be treated or coated to render it more hydrophobic. With such a configuration, overload of sample in the filter chamber will not lead to unfiltered sample circumventing the filter system along the top cover and down around the edge of the filter element insert.

In another preferred embodiment, the top cover can include a recess air channel around and above the edges of the filter compartment. Such a channel, or inverted moat, can present a very large contact angle to fluid from the filter, providing a lateral capillary barrier to spreading of sample, thus limiting the propensity of the sample to leak beyond the boundaries of the filter compartment; particularly, preventing unfiltered sample from flowing around the edge of the filter element.

Filter Elements

The cartridges of the invention typically have a porous filter element housed in a filter chamber. The filter is useful to remove natural constituent particles (e.g., blood cells) or adventitious particles (such as dust) from a sample fluid, so they will not clog cartridge channels or otherwise interfere with the assay.

The filter can be any appropriate type, including, e.g., a perforated membrane, linear or random fiber network material, an open cell foam matrix, and/or the like. In preferred embodiments, the filter element captures larger particles at the top (input) surface and smaller particles at the bottom (output) surface. For example, the filter can have a gradient of smaller pore sizes from the input side to the output side. The filter can be one piece, or include multiple layers. In a more preferred embodiment, the filter includes two layered filters of a course filter overlying a finer filter. In preferred embodiments, the filter has average effective pore sizes (throughout, input and/or output) ranging from 500 μm to 0.1 μm, from 250 μm to 0.2 μm, from 100 μm to 0.5 μm, from 50 μm to 1 μm, or from 20 μm to 10 μm. In preferred embodiments, the average effective filter input pore size is about 250 μm and the average effective filter output pore size is about 10 μm. In a more preferred embodiment the average filter input pore size is about 150 μm and the average effective filter output pore size is about 20 μm.

In some embodiments, the filter is crushed at or adjacent to the filter edge to help control sample and/or filtrate flow. For example, the edge of the filter can be crushed into a V-shape to provide an indented space along the edge, thereby spacing the filter surface further from filter compartment surfaces and minimizing the potential for capillary flows between the compartment and filter surface. In more preferred embodiments, a filter crush zone aligns with a top cover air channel recess (inverted moat) to further hinder fluid flows towards the edge of the filter element.

The filter elements are typically planar with a broad upper sample input surface and with a relatively narrow thickness dimension. The planar input and output surfaces typically range in length and width from 3 cm to 1 mm, from 1 cm to 2 mm, or from 0.5 cm to 3 mm. The filter thickness typically ranges from 5 mm to 0.05 mm, from 3 mm to 0.1 mm, or from 1 mm to 0.25 mm; or about 0.5 mm. The planar length and width dimensions are typically at least 100-fold, 50-fold, 20-fold, 10-fold or 5-fold greater than the filter element thickness dimension.

In preferred embodiments, the net filtrate flow through the filter is perpendicular to the planar filter surfaces. That is, the net filtrate flow through the filter is completely or largely transverse flow. In preferred embodiments, the net working filtration through filters in cartridges of the invention is not a lateral flow. In preferred embodiments, filtrate does not flow from filter edges to down stream channels or chambers.

Samples for filtration in the cartridges of the invention can be any desired type. Typically the samples are environmental samples, biologic samples, medical samples, and the like. For example, samples can include, blood, saliva, plasma, human serum, urine, lymph, CSF, cell culture media, cell culture suspensions, and the like.

In some embodiments, filtrate is drawn from the output side of the filter by contact with a capillary structure. For example, the bottom of the filter compartment can include textured (grooved, dimpled, knobby, ridged) structures that can help move the filtrate to the filter compartment outlet to the incubation chamber. Optionally, the filter output surface can be in contact with a capillary matrix, such as, e.g., a foam or fiber pad, that can wick and direct filtrate toward the incubation chamber.

Incubation Chambers

Sample filtrate can be retained in an incubation chamber for a desired period of time, e.g., to be conditioned or to interact with one or more assay reagents. Incubation chambers can hold filtrate at a desired temperature, mix the filtrate with assay constituents such as buffers, capture analytes, and/or mix the filtrate with active reagents such as reactants, ligands, chromophores, fluorophores, and/or the like.

Incubation chambers of the inventive cartridges typically have at least one capillary scale dimension. In this way, filtrate will tend to fill the chamber volume. Incubation chambers typically have at least one dimension less than 1 mm, less than 0.5 mm, less than 0.2 mm, 0.1 mm or less. In typical embodiments, the chamber is generally planar (e.g., in the same general plane as the cartridge) with a depth less than length and width. The incubation chamber volumes generally range from, e.g., 500 μl to 1 μl, from 100 μl to 2 μl, from 50 μl to 5 μl, or from 20 μl to 10 μl.

In many embodiments, the incubation contains one or more assay reagents. The reagents can be in dried form in the chamber space or coated on the chamber walls. The reagents can be in liquid form. Optionally, reagents can flow into the incubation chamber before, during or after the filtrate enters the chamber. The sample filtrate can enter the incubation chamber and come into contact with the reagents. An analyte in the filtrate can interact with the reagent to form a reaction product. For example, an analyte can be captured by a ligand in solution or a ligand attached to the chamber surface. The analyte can take part in a chemical reaction with the reagent, forming an identifiable product.

The flow of fluid out from the incubation chamber can be controlled by a flow modulator at the outlet of the incubation chamber.

Flow Modulators

Flow modulators can influence the flow rate out of the incubation chamber and thus affect the retention time of filtrate and/or reaction mixture in the chamber. Flow modulators can be any structures that modulate the flow of fluid out of the incubation chamber, e.g., as compared to the flow that would occur with a direct unmodified conduit connection between the incubation chamber and the detection channel. Flow modulators of the invention are typically not mechanical valves, hydrophobic interacting time gates or electrowetting valves. The flow modulators of the invention are typically constrictive (resistive) channels, channels not fully enclosed with capillary interactive surfaces, or flow paths that do not necessarily completely stop flows for a time, but typically reduce flow rates, e.g., to effectively allow completion of a desired incubation time.

In one form, the flow modulator can be a constriction at the incubation chamber output port. The constriction can be a constricted port or a continuing restricted channel. Longer constricted channels can be contorted in patterns that minimize the space required, e.g., a serpentine pattern. In one aspect, the cross sectional area (perpendicular to the direction of fluid flow) in a constricted channel flow modulator can be 0.5, 0.25, 0.1, 0.05 or less of the area of the incubation chamber input port (or, optionally, the output port) or of the detection channel average cross sectional area. For example, where the port or channel has a cross sectional area of 1 $mm^2$, a flow modulator can have a 0.5 $mm^2$, 0.25 $mm^2$, 0.1 $mm^2$, 0.05 $mm^2$ or less. Retaining a similar height dimension between the flow modulator and detection channel and/or incubator chamber offers the advantage of retaining capillarity regardless of volume, and manufacturing simplicity. In many embodiments, although the cross sectional area of the flow modulator is less than the incubation chamber port or the detection channel, at least one cross sectional dimension (preferably the height) is the same. For example in many embodiments, the height dimension of the flow modulator is the same as the height dimension of the incubation chamber or the detection channel, or between 110% to 90% of the height, or between 150% to 75% of the height.

Constriction based flow modulators can slow flow of reaction product fluids from the incubation chamber. However, it can be useful that constrictive flow modulator flow paths can function to provide a biphasic or triphasic flow rate. This previously unrecognized aspect can allow extended incubation at low flows followed by more rapid flows when the reaction product is to be introduced into the detection channel to contact analytical regions. For example, when sample filtrate flows into the incubation chamber, the flow rate can be relatively high. When the filtrate (typically having contacted a reagent in the chamber) enters the constricted flow modulator flow path, the flow through the chamber along its length direction can slow significantly, thus allowing time for efficient reactions or reaction completion. The flow modulator flow path can have a cross-section and length suitable to provide the desired flow delay. Delay of fluid flow reaching the detection channel can be due to the increase in the travel length along the fluid progressing front. Further, without being bound to a particular theory, we believe part of the delay can be due to frictional and viscous resistance through the narrow flow path and part of the resistance to flow can be due to surface tension at the progressing fluid surface front as is moves along the narrow flow path. However, once the desired delay period has been provided, the fluid surface front can proceed, e.g., into the cross section of the detection chamber with lower resistance at a higher flow rate, e.g., possibly due to a lowered resistance to flow offered by the broader flow surface front. Because fluid can flow slower with the fluid front in the constricted channel and faster once the fluid front passes out from the constricted channel, a fast-slow-fast sequence can be provided to control incubation times while expediting the overall analysis.

Figure 4A:
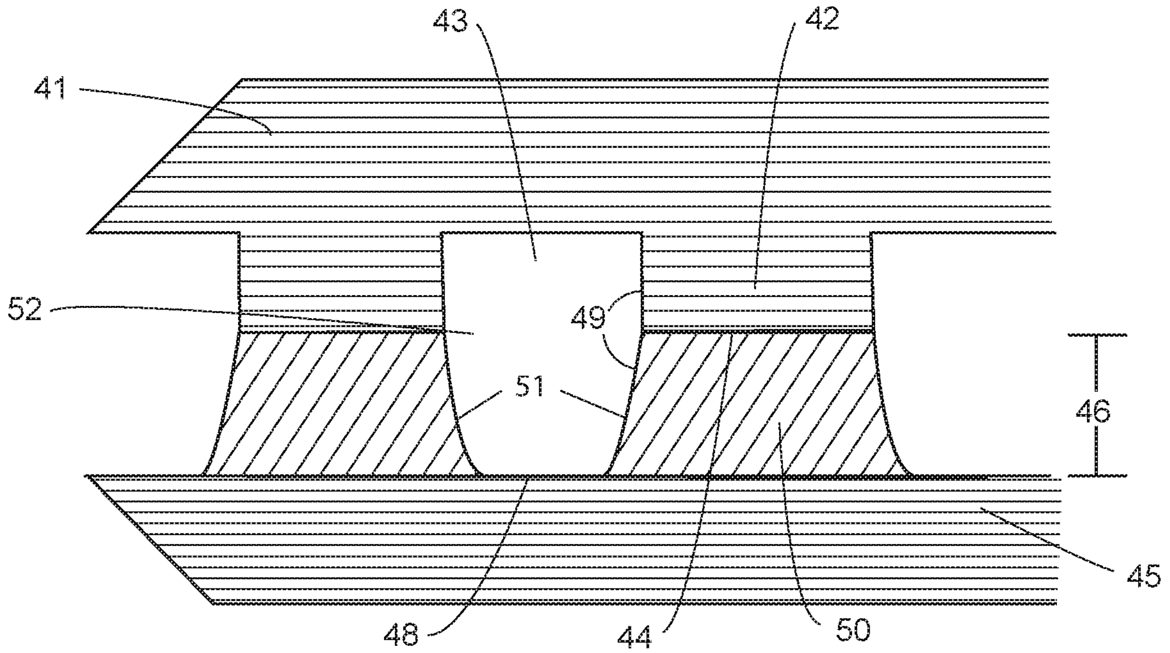
FIGS. 4A and 4B are schematic diagrams showing aspects of a flow modulator including a serpentine flow path without side walls.
Figure 4B:
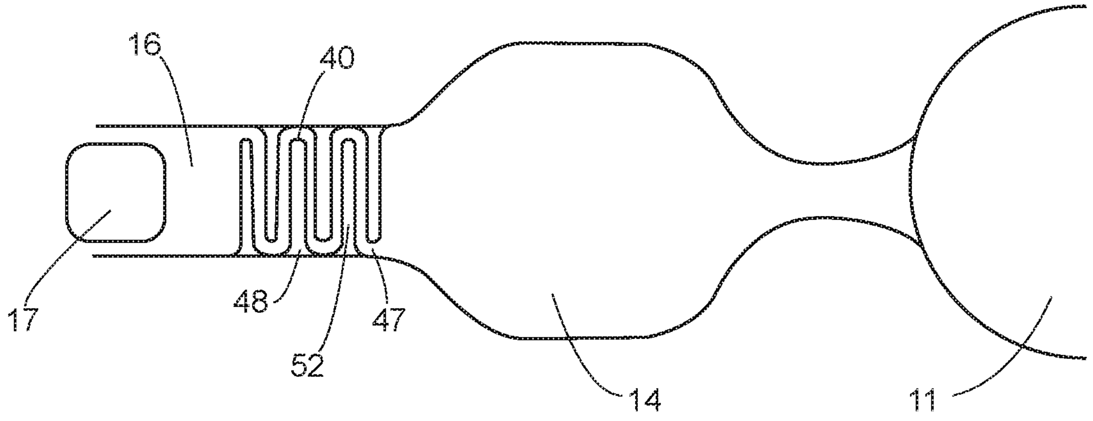

In a most preferred embodiment of flow modulators, the cross section perpendicular to fluid flow is defined on two sides by opposite flow path surfaces and on two sides in between the flow path surfaces by gaseous space. For example, as shown in FIG. 4B, a serpentine flow path 40 can be formed between incubation chamber 14 and detection chamber 16. The path can be defined by path surface projections (e.g., defined by border surface recesses) from the top cover and/or base section. For example, as shown in partial sectional view FIG. 4A, the top cover 41 can include downward processes 42 and/or recesses 43 that define a capillary flow path between the top cover flow path surface 44 and the base section 45 flow path surface. The projections can be spaced from the base section 45 a capillary distance 46. Reaction mixture fluid introduced to the flow modulator input port 47 will flow by capillary action along the flow path, but will not flow laterally across inter-path (lateral space) region 48 due to, e.g., the capillary barrier large contact angle 49 created between the fluid 50 and the slanted or vertical wall edge of the flow path surface 44. Note that the sides 51 of the fluid flow are not enclosed by solid channel structures, but defined and contained by surface tension of the fluid, preventing it from flowing into lateral spaces 52.

Sideless flow paths can be configured a number of ways. Flow paths without flow limiting solid side walls can be defined by flow path surfaces spaced a capillary distance from each other and laterally limited by adjacent lateral spaces with surfaces separated by greater than a capillary distance. That is, e.g., a flow path surface on the bottom of a top cover can be defined by a recessed adjacent surface and/or a flow path surface on the top of a base section can be defined by a recessed adjacent surface. A flow path can be created between the top cover and base section where the flow path surfaces are close enough together to allow capillary flow of a fluid of interest therebetween (a capillary distance). The fluid will not flow laterally into the lateral space because the distance between surfaces is greater and the contact angle where the surface recesses is too great where the slanted or vertical wall creates a high capillary barrier at the edge of flow path. Of course, the capillary distance can vary depending on a particular application. For example, the capillary distance that will allow capillary flow between two opposing flow path surfaces can depend on the nature of the fluid, nature of the surfaces, temperature, slope, affinity between the surfaces and the fluid, hydrostatic pressure on the fluid, and/or the like. In preferred embodiments, the slanted angle of a flow path edge can range from 10 to 90 degrees. In certain embodiments, the internal angle between the flow path surface and the surface over the edge can be less than 90 degrees.

It is envisioned that a flow path can be established between surfaces by providing regions of higher and lower affinity for the fluid of interest. For example, a recessed surface of a lateral space can be made further resistant to lateral flow by providing a lateral space surface with less affinity for the fluid (e.g., a more hydrophobic lateral space surface to contain an aqueous or polar fluid, or a more hydrophilic lateral space surface to contain an organic solvent fluid). In some cases, flow paths can be provided, e.g., between parallel planar surfaces, without recesses, based solely on patterned regions of different hydrophobicity.

These flow modulator structures not only establish an incubation time flow period out of the incubation chamber, but offer further previously unrecognized advantages, such as, e.g., resistance to blockage by air bubbles and reducing required manufacturing and assembly precision of these fine structures. For example, air bubbles escaping the incubation chamber to the flow modulator with reduced cross section, but without side walls, can escape to the air space between the flow path sections without forming a vapor lock in the flow path. Moreover, in the old art of wall enclosed channels and layered cartridges there are edge interfaces of layers that can result in leakage or circumventing capillary flows if the layer interfaces are not perfectly sealed or not precisely aligned. On the other hand, flow paths without side walls in the present invention do not have these problems because the flow path does not include side wall seals or precision aligned layer edge interfaces. The inventive design inherently avoids the problems of bubble blockage, channel sealing and interface capillary flows.

A further previously unrecognized advantage to the flow modulator without side walls is the opportunity to provide efficient cartridge venting. For example, while the incubation chamber is filling, displaced gases can efficiently vent through the large cross section provided by the combined flow path and lateral spaces. Further, a vent port fluidly connecting a lateral space with the external environment can provide venting for the cartridge overall.

In many embodiments of sideless flow modulators, the upper and lower flow path surfaces are in parallel planes. Typically these planes are coplanar with incubator chamber and/or detection channel surfaces, such as top (e.g., top cover) surfaces and bottom (e.g., base section) surfaces. In this way, geometric changes along the flow path do not result in contact angle changes that would disturb the capillary flow of fluids in or out of the flow modulator flow path. Alternately, the height of the flow modulator flow path can be different from the incubation chamber and/or detection channel, e.g., to increase or decrease capillary flow, as desired.

In some embodiments of the inventive cartridges, one or more flow modulators are provided between the incubation chamber and one or more analytical regions in the detection channel. In some embodiments, one or more flow modulators are provided between the one or more analytical regions (and/or substrates) in the detection channel. In some embodiments, one or more flow modulators are provided between two or more incubation chamber and one or more analytical regions in the detection channel. For example, a first flow modulator can be provided between an incubation chamber and a first analytical region in the detection channel. A second flow modulator can be provided, e.g., between the first analytical region and a second analytical region in the detection channel so that desired reaction, detection, or capture interactions can be completed before the fluid goes on to the next analytical region.

In some embodiments, reactions and/or detections take place in the flow modulator. In some assays it can be advantageous to have the incubation reaction product in a small volume, a vented environment, and/or in an environment with a high surface to volume ratio. Sideless capillary channels can be employed to improve fluid mixing. For example, a serpentine constricted channel flow modulator coated with a receptor can efficiently capture its ligand, aided by the long retention time, high surface area and short diffusion distances provided in the channel.

Analytical Regions

Analytical regions are sections along the detection channel where reactions and/or detections take place in association with analysis of a particular analyte. Analytical regions are typically defined by the location of a reagent (including capture molecules) in or on a substrate of the detector channel. Cartridges of the invention typically include more than one analytical region. Although one, two, or more putative analytes of interest may be present to react or incubate together in the incubation chamber, each analytical region can be specialized to function in the analytical scheme for a particular analyte of interest, but not function in the analysis of other analytes of interest.

Analytical regions can be identified as the location of a reagent in or on a porous substrate, or the location of the reagent on a detection channel solid support surface. Reagents can include, e.g., chromogens, affinity molecules, antibodies, monoclonal antibodies, enzymes, enzyme substrates, and/or the like, associated with a particular analytical method.

Analytical regions can function as a first or primary reaction site or capture site for a particular analyte of interest, or may function as a secondary or later reaction or capture site. For example, the analyte of interest can react with a reagent or be captured by a receptor in the incubation chamber, then be captured and/or react at a first or second analytical region.

A single cartridge of the invention can have one, preferably two or more analytical regions. In preferred embodiments, two or more analytical regions are not provided along separate detection channel branches, but are provided sequentially along the same detection channel. Cartridges of the invention can have two or more detection channels, e.g., branching from the same incubation chamber or flow modulator, but it is preferred to have a single detection channel containing all the analytical regions, e.g., along a single porous substrate. A cartridge of the invention can have 1, 2, 3, 4, 5, 6, 7, 8, 9, 10 or more analytical regions. In many cases, each of the analytical regions function in assay and detection of a different analyte of interest.

Analytical regions are provided along a detection channel. The detection channel can receive a liquid fluid from an incubation chamber, e.g., through a flow modulator, for distribution to analytical regions for further incubation, reaction and/or detection. The detection channels can range in length from more than about a meter to less than about a millimeter. In preferred embodiments, the detection channel ranges in length (e.g., in the direction of fluid flow) from about 20 cm to about 2 mm, from 10 cm to 5 mm, from 5 cm to 10 mm, or about 30 mm. In preferred embodiments, the detection channel ranges in width from more than about 5 cm to less than about 0.1 mm, from 1 cm to 0.5 mm, from 5 mm to 1 mm or about 2 mm. In preferred embodiments, the detection channel ranges in height from more than about 5 mm to less than about 0.01 mm, from 2 mm to 0.05 mm, from 1 mm to 0.1 mm or about 0.5 mm. In preferred embodiments, the detection channel is a capillary channel.

Analytical region substrates typically do not fill the cross section of the detection channel across the axis of fluid flow in the analytical region. In a preferred embodiment, the analytical region is located on a substrate of material located on a surface of the detection channel, but not traversing the entire cross section at that location. For example, the analytical region substrate can be located on the floor (e.g., base section surface) of the detection channel extending $1/10^{th}$ of the distance across the channel. In preferred embodiments the analytical region substrates occupy 90% or less, about 80%, 70%, 50%, 25%; or more preferably 15% or less, about 10%, 5%, 2% or less of the detection channel cross section.

An analytical region can comprise a reagent or receptor on the surface of a detection channel without a substrate matrix or without taking up a significant portion of the channel cross section. Alternately, an analytical patch can be associated with a substantially three dimensional substrate structure, preferably a porous substrate, on the inner surface of the detection channel. In preferred embodiments, the analytical region comprises components taking part in analyte reactions or capture. An analytical region can be a defined structure ranging in length (e.g., in the direction of fluid flow) from about 1 cm to about 0.1 mm, from 5 mm to 0.2 mm, from 3 mm to 0.5 mm, or about 2 mm. In preferred embodiments, an analytical region extends all or most the way across the width of the detection channel. For example an analytical region can range in width from more than about 5 cm to less than about 0.1 mm, from 1 cm to 0.5 mm, from 5 mm to 1 mm or about 2 mm. In preferred embodiments, the analytical region substrates range in thickness from more than about 1 mm to less than about 0.005 mm, from 0.5 mm to 0.01 mm, from 0.25 mm to 0.05 mm or about 0.1 mm. In a preferred embodiment, the cross section of the detection channel is about 200 μm (H)×2 mm (W) and the analytical region substrate comprises a 20 μm×2 mm cross section, 2 mm long, layer porous polymer of nitrocellulose on the floor of the detection channel. In preferred embodiments, the analytical patch can have pore sizes ranging from more than about 0.5 mm to less than about 0.005 mm, from 0.2 mm to 0.01 mm, from 0.25 mm to 0.05 mm or about 0.1 mm. The analytical patches are often glued onto the base substrate with an adhesive; or more preferably, coated on the base substrate using thin film deposition, e.g., through chemical vapor deposition or physical vapor deposition; or spin coated onto a detection channel surface.

Analytical region materials can be any suitable materials. In many cases, it is desirable that the analytical region include a substrate matrix that increases the surface area, e.g., to increase the local concentration of associated reagents or capture moieties (receptors and/or ligands). Where a detection takes place at the analytical region based on interrogation by a light beam, it can be preferred that the analytical region substrate, and/or the cartridge material around the detection channel, be transparent to the interrogating light.

In embodiments where two or more analytical regions functionally interact with different analytes (or their associated reaction products), it can be preferred that the reagents and/or capture moieties at the analytical regions be adjusted to provide output signals of similar intensity for expected amounts of each analyte of interest. That is, e.g., where the signal amplitude is high for a reaction product associated with a first analyte at a first analytical region, but the signal amplitude is low for a reaction product associated with a second analyte at a second analytical region, it can be preferred to increase the concentration of reagents at the second analytical region. Such an arrangement can allow a broader range of quantitation and/or sensitivity for each analyte of interest using the same standard detection parameters.

Waste Chambers

Waste chambers can be provided in the cartridges of the invention to receive flow-through fluids from the detection channel. For example, a waste chamber can be a chamber with a volume large enough to receive excess conditioning buffer, sample filtrate, reagents, reaction products, rinse/wash buffers, and the like, that must pass through the detection channels, depending on the particular assay scheme.

A typical waste chamber is a vented chamber of adequate size to receive the expected fluids. The waste chamber can include capillary dimensions to facilitate flow of waste fluid into the chamber by capillary action. Optionally, the waste chamber can include fluid absorbent material, such as, e.g., fibrous pads, foams or hydrophilic polymers, to facilitate the flow and capture of waste fluids.

Analytical Methods Using the Cartridges of the Invention

Methods of the invention include providing a cartridge of the invention, introducing a sample fluid into the cartridge, and detecting one or more analytes of interest.

Cartridges can be provided, as described above. The cartridge can be provided with, e.g., a filtration chamber input port, a vertical flow filter element in the filtration chamber and a filtration chamber outlet port to an incubation chamber. A flow modulator (e.g., a constricted channel and/or a capillary flow path without side walls) can be provided between the incubation chamber and a detection channel comprising one, two, or more analytical regions. On introduction of the sample (e.g., blood, serum, plasma, conditioned media, etc.) to the top of the filter element, interfering particles are removed and sample filtrate flows into the incubation chamber where one or more putative analytes of interest are conditioned (pH adjusted, ionic strength adjusted, blocking agents added, temperature set, etc.), reacted with a reagent, and/or captured by an associated receptor moiety. The flow of incubated fluid from the incubation chamber can be controlled by a flow modulator, which influences the time and/or rate of flow from the incubation chamber to the detection channel.

In the detection channel, one or more analytes can be detected at one or more analytical regions. In embodiments where there are two or more analytes to be determined at two or more analytical regions, it can be preferred to configure the cartridge and/or detection system to provide maximum assay sensitivity and quantitation range for each analyte. As discussed above, the output from an analytical region can be modulated by adjusting the amount of reagent provided at the region. Optionally, the analyte-associated signal detected for each analytical region can be influenced by, e.g., the intensity of interrogation and the sensitivity of the detector. For example, where a strong signal is expected from, e.g., an analytical region having a high concentration of reagent, high concentration of analyte, or a detectable marker with a particularly strong signal, the amplitude of an interrogating light source can be attenuated. Optionally, the sensitivity of the associated detector can be turned down.

In a most preferred embodiment, the analytical regions on the same cartridge are configured to provide a similar range of detection signals for the expected concentrations of analytes. Further, it is preferred to hold the detector sensitivity at a certain value and to adjust for different cartridge assay ranges by adjusting the intensity of the interrogating light source. For example, a universal assay reader can be configured by providing cartridges with matching signal output ranges. A detector (e.g., photomultiplier tube) is provided with a suitable, but unchanging, sensitivity. An adjustable interrogating light source is provided to illuminate the analytical regions with an optimum amount of appropriate light wavelength to provide optimal matching of analytical region output to detector sensitivity. Thereby, desired sensitivity and/or range of quantitation can be obtained for each of multiple analytes and analytical regions on a multi-assay cartridge.

EXAMPLES

The following examples are offered to illustrate, but not to limit the claimed invention.

Example 1—Sandwich Assay

Multiple antigens from the same sample can be detected on the same analytical cartridge. Different analytical regions of the cartridge have solid support (e.g., base section material or porous substrate) bound antibodies against different antigens. A sample that may include one or more of the MHC antigens of interest incubates with a variety of labeled antibodies against the range of the antigens. Then, antigens bound to their specific antibodies are specifically captured by the different solid support bound antibodies at each analytical region. Labeled antibodies held in the analytical regions, through the antigen bound to antibody bound to the support, are detected at the region designated for that antigen. The assay can proceed, as follows:

1) A cartridge is provided with 5 different monoclonal antibodies as a dry composition in the incubation chamber. Each of the monoclonal antibodies is to a different MHC antigen and each antibody is labeled with a fluorophore.
2) A sample of white blood cell lysate is introduced to the upper surface of the cartridge filter element. The filter element comprises a lamination of an upper course depth filter with a 150 μm pore size to a finer lower filter layer having a gradient of pore sizes top to bottom ranging from 100 μm to 10 μm. Cell fragments are removed from the lysate by the filter element to provide a filtrate that flows past an anti-back flow structure into the incubation chamber to contact the dried monoclonal antibodies.
3) The filtrate includes MHC antigens corresponding to 4 of the 5 monoclonal antibodies. The filtrate fills the incubation chamber and dissolves the dried antibodies. When the filtrate contacts the flow modulator at the output port of the incubation chamber, the flow rate of filtrate into the incubation chamber slows. Due to the slower flow rate through the flow modulator, the filtrate resides in the incubation chamber for a time adequate for binding between monoclonal antibodies and their corresponding antigens to reach equilibration.
4) Flow through the flow modulator proceeds to the point where the fluid begins to exit the flow modulator into the detection channel. The rate of flow increases somewhat as the fluid front enters the larger cross section of the detection channel.
5) The mixture of antigens bound to antibodies in the filtrate flows over 5 different analytical regions in sequence along the detection channel solid support. Each of the regions includes a different capture antibody bound in excess to a nitrocellulose substrate. Antigens bound to labeled monoclonal antibodies are captured by the appropriate capture antibody, in the manner of a "sandwich" assay, resulting in a bound chain of labeled antibody-antigen-capture antibody-solid support. No labeled antibody is captured for the instance in which the associated antigen was not present in the original cell lysate.
6) Excess filtrate passes over the analytical regions, washing away excess labeled antibody that is not bonded to the antigen.
7) The analytical regions are illuminated sequentially with an excitation wavelength light from a laser. The presence, or absence, of emission wavelengths is detected at each analytical region corresponding to each particular putative MHC antigen of interest.

Example 2—Universal Detection System

Cartridges for detection of different types of analytes, having substantially different detectable signals, can be read using the same detection system. Two different assay cartridges with different arrays of analytical regions and different signal intensities from detectable labels are analyzed using the same detector system. Cartridges are adjusted to provide approximately similar readable output ranges among the analytical regions associated with multiple analytes to be assayed on the cartridges. The cartridges include a code readable by the detector identifying the expected signal intensity range for each cartridge. The detector system configures the illumination intensity to an amplitude expected to optimize sensitivity and/or useful quantitation range for analytes on the currently scanned cartridge. The assay system can be configured as follows to provide reading of diverse assays on a universal cartridge reading system:

1) Determine the useful detectable signal strengths for each of the analytes to be analyzed on the same cartridge. Adjust the concentration of analytical region reagents and/or capture molecules to provide approximately equivalent output signals from each analytical region, e.g., based on the expected range of each analyte in a sample of interest.

2) Determine a light illumination intensity that will provide the desired sensitivity and/or range of outputs detectable by the system detector device.

3) Provide a barcode reader on the detector system. Provide a barcode on the cartridge readable by the barcode reader to provide the determined light illumination intensity to the detector system.

4) Provide a light source (e.g., laser) in the detector system that is capable of at least a $10^3$-fold intensity variation, with the maximum output at least the minimum required intensity for any cartridge intended to be scanned.

5) Provide a computer in, or associated with, the detector system that can interpret the barcode reader output and send a command to the light source setting the illumination intensity to the determined amplitude for the particular cartridge.

Example 3—Porous Substrate Analytical Regions

A cartridge was prepared with a porous substrate in the detection channel.

Figure 5:
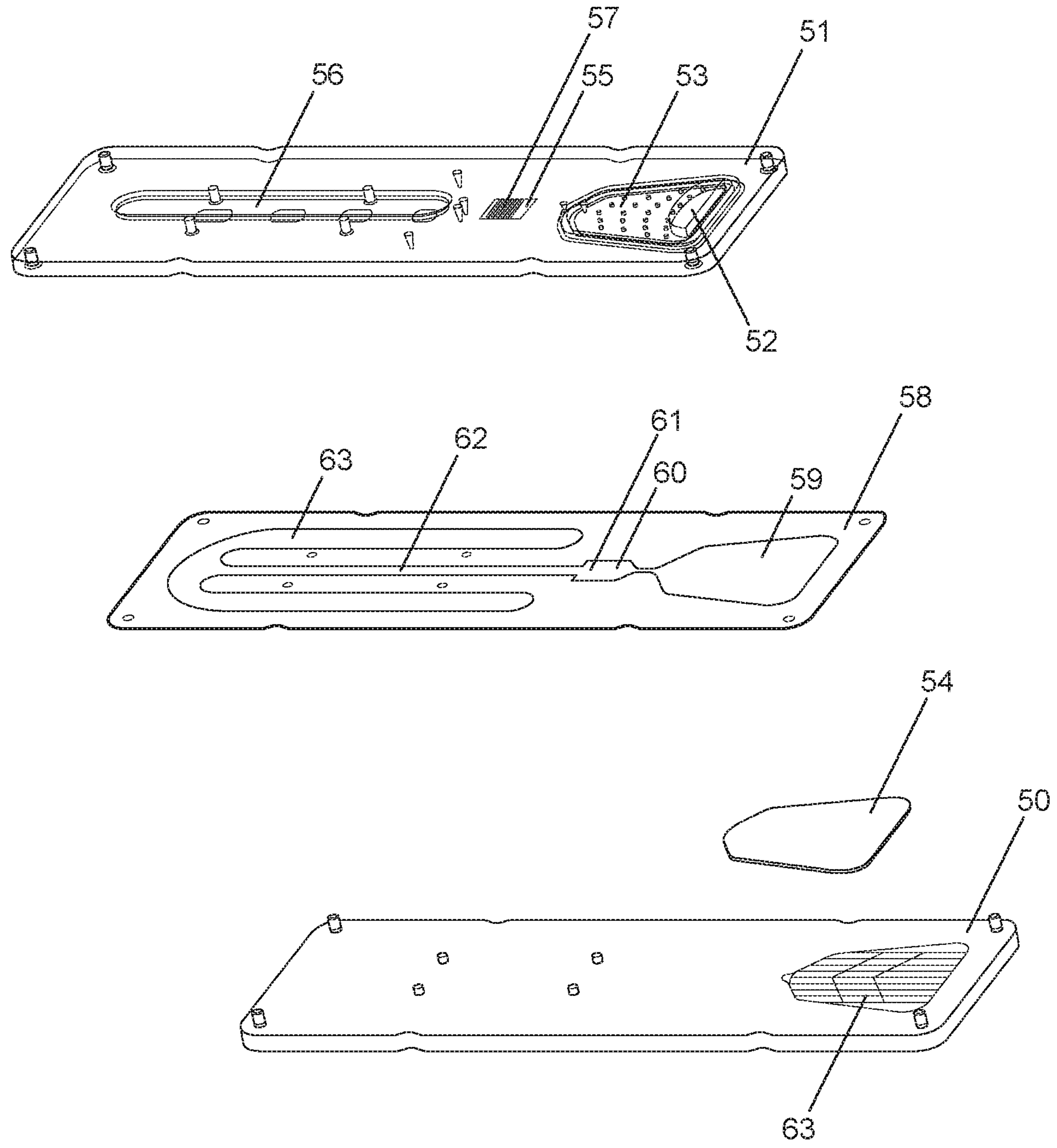
FIG. 5 is a schematic diagram depicting an exploded view of an exemplary analytical cartridge having an open lateral wall flow modulator and analytical regions on a porous substrate.

The cartridge, essentially as shown in FIG. 5, included a bottom section 50 with a relatively flat surface, but for capillary flow enhancing groves 63 in the filter area, and alignment pegs complimentary to holes in the top cover 51.

The top cover included most of the topographic features of the chip, including, e.g., the sample loading inlet 52, an upward filter recess 53 to receive much of the filter 54 height, an upward reaction recess 55 to expand the volume of the incubation (reaction) chamber, an upward detection recess 56 to increase the detection channel volume and slow flow through the detection channel, and recesses leaving unrecessed surfaces 57 (not shown here in detail) defining serpentine capillary channel flow path (flow modulator).

Two sided tape membrane 58 with excised areas acted as the membrane layer between the bottom section and top cover. Excised areas provided all or part of the chambers or channels of the chip. For example, the membrane layer included an excised filter region 59, a reaction/incubation region 60, a flow modulator region 61, a detector region 62, and a waste capillary region 63.

To provide a porous substrate in the detection region, nitrocellulose in a solvent suspension was introduced to the top surface of the bottom section while it was being spun in a plane perpendicular to the top surface. Excess nitrocellulose solution was flung from the surface leaving a uniform coating on the entire surface. The solution was wiped from surfaces where not desired, but left at least in the area of the detection channel. The nitrocellulose was allowed to dry, leaving a porous substrate less than the assembled height of the detection channel.

Analytical regions were provided on the porous substrate by application of capture antibodies to the nitrocellulose at desired positions along the channel. The antibodies were bound to the nitrocellulose. The porous substrate was treated with a blocking agent to reduce the possibility of non-specific binding during an analyses.

It is understood that the examples and embodiments described herein are for illustrative purposes only and that various modifications or changes in light thereof will be suggested to persons skilled in the art and are to be included within the spirit and purview of this application and scope of the appended claims.

While the foregoing invention has been described in some detail for purposes of clarity and understanding, it will be clear to one skilled in the art from a reading of this disclosure that various changes in form and detail can be made without departing from the true scope of the invention. For example, many of the techniques and apparatus described above can be used in various combinations.

All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. An analytical cartridge comprising:

a sample input port in fluid communication with an incubation chamber through a capillary channel;

two or more separate detection channel branches in fluid contact with the incubation chamber;

one or more analytical regions in each detection channel branch, wherein a first analytical region in a first of the separate detection channel branches is adapted to detect a first analyte, and a second analytical region in a second of the separate detection channel branches is adapted to detect a second analyte different from the first analyte.

2. The analytical cartridge of claim 1, further comprising a filter in the sample input port.

3. The analytical cartridge of claim 1, wherein the incubation chamber comprises an analytical reagent or an affinity molecule.

4. The analytical cartridge of claim 1, wherein the incubation chamber is wider than the first capillary channel.

5. The analytical cartridge of claim 1, wherein a first of the detection channel branches comprises an analytical reagent or an affinity molecule.

6. The analytical cartridge of claim 1, wherein a second of the detection channel branches comprises an analytical reagent or an affinity molecule different from that of the first detection channel.

7. The analytical cartridge of claim 1, further comprising a cartridge top cover and a cartridge base both made of transparent materials allowing interrogation of analytical regions by an external detector light source.

8. The analytical cartridge of 1 wherein an analytical region comprises a porous substrate disposed on a top or bottom surface of the first detection channel, and wherein a cross sectional area of the porous substrate at the one or more analytical regions is less than 90% of the total channel cross sectional area in a plane perpendicular to the channel axis.

9. An assay reader system comprising the analytical cartridge of claim 1, an interrogating light source adapted to illuminate the one of more analytical regions, and a detector adapted to detect a signal from the one or more analytical regions.

10. An assay reader system of claim 9, wherein the interrogating light source is adapted to provide two or more selectable intensities of illumination.

11. A method of sample analysis, the method comprising:

applying a liquid sample to the input port of the cartridge of claim 1;

flowing the sample by capillary action through the capillary to the incubation chamber;

reacting one of more analytes of the sample with a reagent or affinity molecule in the incubation chamber;

flowing reacted sample to the to the first and second detection channel branches; and, detecting the presence of reacted analyte at an analytical region of the first or second detection channel branch.

12. The method of claim 11, further comprising detecting a different analyte in the first detection channel branch than in the second detection channel branch.

13. The analytical cartridge of claim 1, wherein the incubation chamber is downstream from the sample input port and upstream from each of the two or more separate detection channel branches.

14. The analytical cartridge of claim 1, wherein both the incubation chamber and the one or more analytical regions of a detection channel branch comprise one or more reagents or affinity molecules.

* * * * *